US012618073B1

(12) United States Patent
Thompson

(10) Patent No.: US 12,618,073 B1
(45) Date of Patent: May 5, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 19/319,418

(22) Filed: Sep. 4, 2025

(51) Int. Cl.
*C12N 15/113* (2010.01)
*C12N 15/86* (2006.01)

(52) U.S. Cl.
CPC .......... *C12N 15/1138* (2013.01); *C12N 15/86* (2013.01); *C12N 2310/141* (2013.01); *C12N 2750/14143* (2013.01)

(58) Field of Classification Search
CPC ................ C12N 15/86; C12N 15/1138; C12N 2310/141; C12N 2350/14143
See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 | 11/2021 | Minshull et al. | |
| 11,530,423 B1 | 12/2022 | Thompson | |
| 11,873,505 B2 | 1/2024 | Thompson | |
| 12,018,274 B2 | 6/2024 | Thompson | |
| 12,134,770 B1 | 11/2024 | Thompson | |
| 12,435,338 B2 * | 10/2025 | Thompson | C12N 15/113 |
| 2024/0026377 A1 | 1/2024 | Thompson | |

FOREIGN PATENT DOCUMENTS

CA          2721333 A1    10/2009

OTHER PUBLICATIONS

U.S. Appl. No. 19/300,113 (Year: 2025).*
Bottoni et al. "Targeting BTK through microRNA in chronic lymphocytic leukemia." Blood, The Journal of the American Society of Hematology 128.26 (2016): 3101-3112.
Brutons Tyrosine Kinase Genbank Sequence (2023).
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Van den Berg, et al., pp. 1-12, Molecular Therapy—Nucleic Acids, vol. 5, 2016 (Year: 2016).

Nature (2010. Gene Expression. Scitable. Available online at Nature. com) <https://www.nature.com/scitable/topicpage/gene-expression-14121669> (2010).
GenBank EGF Sequence (2023).
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
NCBI search results for SEQ ID No. 5 (2024).
NCBI Nucleotide Sequence ALK Lingand, search performed Dec. 26, 2024 (2023).
NCBI Nucleotide Sequence ALK Receptor, search performed Dec. 26, 2024 (2023).
GenBank EGFR Sequence (2023).
Genbank FLT3 Sequence (2024).
NCBI Nucleotide Sequence for PARP, search performed Dec. 26, 2024 (2024).
Tritschler et al. "Concepts and limitations for learning developmental trajectories from single cell genomics." Development 146.12 (2019): dev170506.
Kondratov et al. "Direct head-to-head evaluation of recombinant adeno-associated viral vectors manufactured in human versus insect cells." Molecular Therapy 25.12 (2017): 2661-2675.
O'Brien et al. Overview of MicroRNA Biogenesis, Mechanisms of Actions, and Circulation, Frontiers in Endocrinology, vol. 9, Article 402: 1-12 (2018). (Year: 2018).
Gorski, S., Vogel, J. & Doudna, J. RNA-based recognition and targeting: sowing the seeds of specificity. Nat Rev Mol Cell Biol 18, 215-228 (2017). (Year: 2017).
Denzler R et al. Impact of MicroRNA Levels, Target-Site Complementarity, and Cooperativity on Competing Endogenous RNA-Regulated Gene Expression. Mol Cell. Nov. 3, 2016;64(3):565-579. doi: 10.1016/j.molcel.2016.09.027 (Year: 2016).
Wang et al. "Adeno-associated virus vector as a platform for gene therapy delivery". Nat Rev Drug Discov. May 2019;18(5):358-378. (Year: 2019).

* cited by examiner

*Primary Examiner* — Jane J Zara
(74) *Attorney, Agent, or Firm* — Gowling WLG (Canada) LLP

(57) ABSTRACT

The embodiments of the present disclosure relate to one or more compositions or methods that upregulate the production of one or more sequences of micro-interfering ribonucleic acid (miRNA). The sequences of miRNA may be complimentary to a sequence of target messenger RNA (mRNA) that encodes for the translation of a target biomolecule, such as platelet-derived growth factor receptor beta (PDGFRB). The miRNA can cause the target mRNA to be degraded or inactivated, thereby causing a decrease in bioavailability of the target biomolecule because it is degraded or inactivated by the miRNA. Decreasing the bioavailability of the target biomolecule within a subject that is administered the one or more compositions may address the afflictions experienced by the subject due to expression of the target biomolecule.

3 Claims, No Drawings

Specification includes a Sequence Listing.

SEQUENCE LISTING

```
Sequence total quantity: 3
SEQ ID NO: 1            moltype = DNA   length = 5807
FEATURE                 Location/Qualifiers
source                  1..5807
                        mol_type = other DNA
                        organism = synthetic construct
SEQUENCE: 1
tctagaataa tcaacctctg gattacaaaa tttgtgaaag attgactggt attcttaact   60
atgttgctcc ttttacgcta tgtggatacg ctgctttaat gcctttgtat catgctattg  120
cttcccgtat ggctttcatt ttctcctcct tgtatataatc ctggttgctg tctctttatg 180
aggagttgtg gcccgttgtc aggcaacgtg gcgtggtgtg cactgtgttt gctgacgcaa  240
cccccactgg ttggggcatt gccaccacct gtcagctcct ttccgggact ttcgctttcc  300
ccctccctat tgccacggcg gaactcatcg ccgcctgcct tgcccgctgc tggacagggg  360
ctcggctgtt gggcactgac aattccgtgg tgttgtcggg gaaatcatcg tcctttcctt  420
ggctgctcgc ctgtgttgcc acctggattc tgcgcgggac gtccttctgc tacgtccctt  480
cggccctcaa tccagcggac cttccttccc gcggcctgct gccggctctg cggcctcttc  540
cgcgtcttcg ccttcgccct cagacgagtc ggatctccct ttgggccgcc tccccgccta  600
agcttatcga taccgtcgag atctaacttg tttattgcag cttataatgg ttacaaataa  660
agcaatagca tcacaaattt cacaaataaa gcatttttttt cactgcattc tagttgtggt  720
ttgtccaaac tcatcaatgt atcttatcat gtctggatct cgacctcgac tagagcatgg  780
ctacgtagat aagtagcatg gcgggttaat cattaactac aaggaacccc tagtgatgga  840
gttggccact ccctctctgc gcgctcgctc gctcactgag gccgggcgac caaaggtcgc  900
ccgacgcccg ggctttgccc gggcggcctc agtgagcgag cgagcgcgca gctggcgtaa  960
tagcgaagag gcccgcaccg atcgccttc ccaacagttg cgcagcctga atggcgaatg  1020
gcgattccgt tgcaatggct ggcggtaata ttgttctgga tattaccagc aaggccgata  1080
gtttgagttc ttctactcag gcaagtgatg ttattactaa tcaaagaagt attgcgacaa  1140
cggttaattt gcgtgatgga cagactcttt tactcggtgg cctcactgat tataaaaaca  1200
cttctcagga ttctggcgta ccgttcctgt ctaaaatccc tttaatcggc ctcctgttta  1260
gctcccgctc tgattctaac gaggaaagca cgttatacgt gctcgtcaaa gcaaccatag  1320
tacgcgccct gtagcggcgc attaagcgcg gcgggtgtgg tggttacgcg cagcgtgacc  1380
gctacacttg ccagcgccct agcgcccgct cctttcgctt tcttcccttc ctttctcgcc  1440
acgttcgccg gctttccccg tcaagctcta aatcgggggc tccctttagg gttccgattt  1500
agtgctttac ggcacctcga ccccaaaaaa cttgattagg gtgatggttc acgtagtgga  1560
ccatcgccct gatagacggt ttttcgccct ttgacgttgg agtccacgtt ctttaatagt  1620
ggactcttgt tccaaactgg aacaacactc aaccctatct cggtctattc ttttgattta  1680
taagggattt tgccgatttc ggcctattgg ttaaaaaatg agctgattta acaaaaattt  1740
aacgcgaatt ttaacaaaat attaacgttt acaatttaaa tatttgctta tacaatcttc  1800
ctgtttttgg ggcttttctg attatcaacc ggggtacata tgattgacat gctagtttta  1860
cgattaccgt tcatcgattc tcttgtttgc tccagactct caggcaatga cctgatagcc  1920
tttgtagaga cctctcaaaa atagctaccc tctccggcat gaatttatca gctagaacgg  1980
ttgaatatca tattgatggt gatttgactg tctccggcct ttctcacccg tttgaatctt  2040
tacctacaca ttactcaggc attgcattta aaatatatga gggtctaaa aatttttatc  2100
cttgcgttga aataaaggct tctcccgcaa aagtattaca gggtcataat gtttttggta  2160
caaccgattt agctttatgc tctgaggctt tattgcttaa ttttgctaat tctttgcctt  2220
gcctgtatga tttattggat gttggaattc ctgatgcggt attttctcct tacgcatctg  2280
tgcggtattt cacaccgcat atggtgcact ctcagtacaa tctgctctga tgccgcatag  2340
ttaagccagc cccgacaccc gccaacaccc gctgacgcgc cctgacgggc ttgtctgctc  2400
ccggcatccg cttacagaca agctgtgacc gtctccggga gctgcatgtg tcagaggttt  2460
tcaccgtcat caccgaaacg cgcgagacga aagggcctcg tgatacgcct attttttatag  2520
gttaatgtca tgataataat ggtttcttag acgtcaggtg gcacttttcg gggaaatgtg  2580
cgcggaaccc ctatttgttt attttttctaa atacattcaa atatgtatcc gctcatgaga  2640
caataaccct gataaatgct tcaataatat tgaaaaagga agagtatgag tattcaacat  2700
ttccgtgtcg cccttattcc cttttttgcg gcattttgcc ttcctgtttt tgctcacccca  2760
gaaacgctgg tgaaagtaaa agatgctgaa gatcagttgg gtgcacgagt gggttacatc  2820
gaactggatc tcaacagcgg taagatcctt gagagttttc gccccgaaga cgttttccaa  2880
atgatgagca cttttaaagt tctgctatgt ggcgcggtat tatcccgtat tgacgccggg  2940
caagagcaac tcggtcgccg catacactat tctcagaatg acttggttga gtactcacca  3000
```

-continued

```
gtcacagaaa agcatcttac ggatggcatg acagtaagag aattatgcag tgctgccata   3060
accatgagtg ataacactgc ggccaactta cttctgacaa cgatcggagg accgaaggag   3120
ctaaccgctt ttttgcacaa catgggggat catgtaactc gccttgatcg ttgggaaccg   3180
gagctgaatg aagccatacc aaacgacgag cgtgacacca cgatgcctgt agcaatggca   3240
acaacgttgc gcaaactatt aactggcgaa ctacttactg tagcttcccg gcaacaatta   3300
atagactgga tggaggcgga taaagttgca ggaccacttc tgcgctcggc ccttccggct   3360
ggctggttta ttgctgataa atctggagcc ggtgagcgtg ggtctcgcgg tatcattgca   3420
gcactggggc cagatggtaa gccctcccgt atcgtagtta tctacacgac ggggagtcag   3480
gcaactatgg atgaacgaaa tagacagatc gctgagatag gtgcctcact gattaagcat   3540
tggtaactgt cagaccaagt ttactctatat atactttaga ttgatttaaa acttcatttt   3600
taatttaaaa ggatctaggt gaagatcctt tttgataatc tcatgaccaa aatcccttaa   3660
cgtgagtttt cgttccactg agcgtcagac cccgtagaaa agatcaaagg atcttcttga   3720
gatccttttt ttctgcgcgt aatctgctgc ttgcaaacaa aaaaaccacc gctaccagcg   3780
gtggtttgtt tgccggatca agagctacca actctttttc cgaaggtaac tggcttcagc   3840
agagcgcaga taccaaatac tgtccttcta gtgtagccgt agttaggcca ccacttcaag   3900
aactctgtag caccgcctac atacctcgct ctgctaatcc tgttaccagt ggctgctgcc   3960
agtggcgata agtcgtgtct taccgggttg gactcaagac gatagttacc ggataaggcg   4020
cagcggtcgg gctgaacggg gggttcgtgc acacagccca gcttggagcg aacgacctac   4080
accgaactga gatacctaca gcgtgagcta tgagaaagcg ccacgcttcc cgaagggaga   4140
aaggcggaca ggtatccggt aagcggcagg gtcggaacag gagagcgcac gagggagctt   4200
ccagggggaa acgcctggta tctttatagt cctgtcgggt ttcgccacct ctgacttgag   4260
cgtcgatttt tgtgatgctc gtcaggggggg cggagcctat ggaaaaacgc cagcaacgcg   4320
gcctttttac ggttcctggc cttttgctgg ccttttgctc acatgttctt tcctgcgtta   4380
tcccctgatt ctgtggataa ccgtattacc gcctttgagt gagctgatac cgctcgccgc   4440
agccgaacga ccgagcgcag cgagtcagtg agcgaggaag cggaagagcg cccaatacgc   4500
aaaccgcctc tccccgcgcg ttggccgatt cattaatgca gcagctggca cgacaaccta   4560
tcactgagcc cgcccgggca aagcccgggc gtcgggcgac ctttggtcgc cggcctcag   4620
tgagcgagcg agcgcgcaga gagggagtgg ccaactccat cactagggggt tccttgtagt   4680
taatgattaa cccgccatgc tacttatcta cgtagccatg ctctaggaca ttgattattg   4740
actagtggag ttccgcgtta cataacttac ggtaaatggc ccgcctggct gaccgcccaa   4800
cgacccccgc ccattgacgt caataatgac gtatgttccc atagtaacgc caataggggac   4860
tttccattga cgtcaatggg tggagtattt acggtaaact gcccacttgg cagtacatca   4920
agtgtatcat atgccaagta cgccccctat tgacgtcaat gacggtaaat ggcccgcctg   4980
gcattatgcc cagtacatga ccttatggga ctttcctact tggcagtaca tctacgtatt   5040
agtcatcgct attaccatgg tcgaggtgag ccccacgttc tgcttcactc tccccatctc   5100
ccccccctcc ccaccccaa ttttgtattt atttattttt taattatttt gtgcagcgat   5160
gggggcgggg gggggggggg gcgcgcgcca ggcggggcgg ggcggggcga ggggcggggc   5220
ggggcgaggc ggagaggtgc ggcggcagcc aatcagagcg cgcgctccg aaagtttcct   5280
tttatggcga gcgcgcgacg gcggcggccc tataaaaagc gaagcgcgcg gcgggcggga   5340
gtcgctgcgc gctgccttcg ccccgtgccc cgctccgccg ccgcctcgcg ccgcccgccc   5400
cggctctgac tgaccgcgtt actaaaacag gtaagtccgg cctccgcgcc gggttttggc   5460
gcctcccgcg ggcgcccccc tcctcacggc gagcgctgcc acgtcagacg aagggcgcag   5520
cgagcgtcct gatccttccg cccggacgct caggacagcg gcccgctgct cataagactc   5580
ggccttagaa ccccagtatc agcagaagga cattttagga cgggacttgg gtgactctag   5640
ggcactggtt ttctttccag agagcggaac aggcgaggaa aagtagtccc ttctcggcga   5700
ttctgcggag ggatctccgt ggggcggtga acgccgatga tgcctctact aaccatgttc   5760
atgttttctt ttttttttcta caggtcctgg gtgacgaaca gggtacc               5807
```

```
SEQ ID NO: 2            moltype = DNA  length = 532
FEATURE                 Location/Qualifiers
source                  1..532
                        mol_type = other DNA
                        organism = synthetic construct
SEQUENCE: 2
gccaccatgg ccaccggctc tcgcacaagc ctgctgctgg ctttcggact gctgtgcctg    60
ccttggctcc aggagggctc cgccgctagc atcgataccg tcgctatgtg ctggaggctt   120
gctgaaggct gtatgctgaa cagttcttct gcgcatcgtt cgtttttggcc tctgactgac   180
gaacgatgcg gaagaactgt tcaggacaca aggcctgtta ctagcactca catggaacaa   240
atggcctcta gcctggaggc ttgctgaagg ctgtatgctg acataatacg catatcgcta   300
tccgttttgg cctctgactg acggatagcg atgctgatta tgtcaggaca caaggcctgt   360
tactagcact cacatggaac aaatggcctc tagcctggag gcttgctgaa ggctgtatgc   420
tgtttcttct tcgaactgct gttgcgtttt ggcctctgac tgacgcaaca gcagcgaaga   480
agaaacagga cacaaggcct gttactagca ctcacatgga acaaatggcc tc            532
```

```
SEQ ID NO: 3            moltype = DNA  length = 6339
FEATURE                 Location/Qualifiers
source                  1..6339
                        mol_type = other DNA
                        organism = synthetic construct
SEQUENCE: 3
tctagaataa tcaacctctg gattacaaaa tttgtgaaag attgactggt attcttaact    60
atgttgctcc ttttacgcta tgtggatacg ctgctttaat gcctttgtat catgctattg   120
cttccccgtat ggctttcatt ttctcctcct tgtatataaatc ctggttgctg tctctttatg   180
aggagttgtg gcccgttgtc aggcaacgtg gcgtggtgtg cactgtgttt gctgacgcaa   240
cccccactgg ttggggcatt gccaccacct gtcagctcct ttccgggact ttcgctttcc   300
ccctccctat tgccacggcg gaactcatcg ccgcctgcct tgcccgctgc tggacagggg   360
ctcggctgtt gggcactgac aattccgtgg tgttgtcggg gaaatcatcg tcctttcctt   420
ggctgctcgc ctgtgttgcc acctggattc tgcgcgggac gtccttctgc tacgtccctt   480
cggccctcaa tccagcggac cttccttccc gcggcctgct gccggctctg cggcctcttc   540
```

-continued

```
cgcgtcttcg ccttcgccct cagacgagtc ggatctccct ttgggccgcc tccccgccta    600
agcttatcga taccgtcgag atctaacttg tttattgcag cttataatgg ttacaaataa    660
agcaatagca tcacaaattt cacaaataaa gcattttttt cactgcattc tagttgtggt    720
ttgtccaaac tcatcaatgt atcttatcat gtctggatct cgacctcgac tagagcatgg    780
ctacgtagat aagtagcatg gcgggttaat cattaactac aaggaacccc tagtgatgga    840
gttggccact ccctctctgc gcgctcgctc gctcactgag gccgggcgac caaaggtcgc    900
ccgacgcccg ggctttgccc gggcggcctc agtgagcgag cgagcgcgca gctggcgtaa    960
tagcgaagag gcccgcaccg atcgcccttc ccaacagttg cgcagcctga atggcgaatg   1020
gcgattccgt tgcaatggct ggcggtaata ttgttctgga tattaccagc aaggccgata   1080
gtttgagttc ttctactcag gcaagtgatg ttattactaa tcaaagaagt attgcgacaa   1140
cggttaattt gcgtgatgga cagactcttt tactcggtgg cctcactgat tataaaaaca   1200
cttctcagga ttctggcgta ccgttcctgt ctaaaatccc tttaatcggc ctcctgttta   1260
gctcccgctc tgattctaac gaggaaagca cgttatacgt gctcgtcaaa gcaaccatag   1320
tacgcgccct gtagcggcgc attaagcgcg gcgggtgtgg tggttacgcg cagcgtgacc   1380
gctacacttg ccagcgccct agcgcccgct ccttttcgct tcttcccttc ctttctcgcc   1440
acgttcgccg gctttccccg tcaagctcta aatcggggggc tccctttagg gttccgattt   1500
agtgctttac ggcacctcga ccccaaaaaa cttgattagg gtgatggttc acgtagtggg   1560
ccatcgccct gatagacggt ttttcgccct tgacgttggg agtccacgtt ctttaatagt   1620
ggactcttgt tccaaactgg aacaacactc aaccctatct cggtctattc ttttgattta   1680
taagggattt tgccgatttc ggcctattgg ttaaaaaatg agctgattta acaaaaattt   1740
aacgcgaatt ttaacaaaat attaacgttt acaatttaaa tatttgctta tacaatcttc   1800
ctgtttttgg ggcttttctg attatcaacc ggggtacata tgattgacat gctagtttta   1860
cgattaccgt tcatcgattc tcttgtttgc tccagactct caggcaatga cctgatagcc   1920
tttgtagaga cctctcaaaa atagctaccc tctccggcat gaatttatca gctagaacgg   1980
ttgaatatca tattgatggt gatttgactg tctccggcct ttctcacccg tttgaatctt   2040
tacctacaca ttactcaggc attgcattta aaatatatga gggttctaaa aatttttatc   2100
cttgcgttga aataaaggct tctccccgcaa aagtattaca gggtcataat gtttttggta   2160
caaccgattt agctttatgc tctgaggctt tattgcttaa ttttgctaat tctttgcctt   2220
gcctgtatga tttattggat gttggaattc ctgatgcggt attttctcct tacgcatctg   2280
tgcggtattt cacaccgcat atggtgcact ctcagtacaa tctgctctga tgccgcatag   2340
ttaagccagc cccgacaccc gccaacaccc gctgacgcgc cctgacgggc ttgtctgctc   2400
ccggcatccg cttacagaca agctgtgacc gtctccggga gctgcatgtg tcagaggttt   2460
tcaccgtcat caccgaaacg cgcgagacga aagggcctcg tgatacgcct attttttatag   2520
gttaatgtca tgataataat ggtttcttag acgtcaggtg gcactttttcg gggaaatgtg   2580
cgcggaaccc ctatttgttt attttttctaa atacattcaa atatgtatcc gctcatgaga   2640
caataaccct gataaatgct tcaataatat tgaaaaagga agagtatgag tattcaacat   2700
ttccgtgtcg cccttattcc ctttttttgcg gcattttgcc ttcctgtttt tgctcaccca   2760
gaaacgctgg tgaaagtaaa agatgctgaa gatcagttgg gtgcacgagt gggttacatc   2820
gaactggatc tcaacagcgg taagatcctt gagagttttc gccccgaaga acgttttcca   2880
atgatgagca cttttaaagt tctgctatgt ggcgcggtat tatcccgtat tgacgccggg   2940
caagagcaac tcggtcgccg catacactat tctcagaatg acttggttga gtactcacca   3000
gtcacagaaa agcatcttac ggatggcatg acagtaagag aattatgcag tgctgccata   3060
accatgagtg ataacactgc ggccaactta cttctgacaa cgatcggagg accgaaggag   3120
ctaaccgctt ttttgcacaa catgggggat catgtaactc gccttgatcg ttgggaaccg   3180
gagctgaatg aagccatacc aaacgacgag cgtgacacca cgatgcctgt agcaatggca   3240
acaacgttgc gcaaactatt aactggcgaa ctacttactc tagcttcccg gcaacaatta   3300
atagactgga tggaggcgga taaagttgca ggaccacttc tgcgctcggc ccttccggct   3360
ggctggttta ttgctgataa atctggagcc ggtgagcgtg ggtctcgcgg tatcattgca   3420
gcactggggc cagatggtaa gccctcccgt atcgtagtta tctacacgac ggggagtcag   3480
gcaactatgg atgaacgaaa tagacagatc gctgagatag gtgcctcact gattaagcat   3540
tggtaactgt cagaccaagt ttactcatat atactttaga ttgatttaaa acttcatttt   3600
taatttaaaa ggatctaggt gaagatcctt tttgataatc tcatgaccaa aatcccttaa   3660
cgtgagtttt cgttccactg agcgtcagac cccgtagaaa agatcaaagg atcttcttga   3720
gatcctttttt ttctgcgcgt aatctgctgc ttgcaaacaa aaaaaccacc gctaccagcg   3780
gtggtttgtt tgccggatca agagctacca actctttttc cgaaggtaac tggcttcagc   3840
agagcgcaga taccaaatac tgtccttcta gtgtagccgt agttaggcca ccacttcaag   3900
aactctgtag caccgcctac atacctcgct ctgctaatcc tgttaccagt ggctgctgcc   3960
agtggcgata agtcgtgtct taccgggttg gactcaagac gatagttacc ggataaggcg   4020
cagcggtcgg gctgaacggg gggttcgtgc acacagccca gcttggagcg aacgacctac   4080
accgaactga gatacctaca gcgtgagcta tgagaaagcg ccacgcttcc cgaagggaga   4140
aaggcggaca ggtatccggt aagcggcagg gtcggaacag gagagcgcac gagggagctt   4200
ccagggggaa acgcctggta tctttatagt cctgtcgggt ttcgccacct ctgacttgag   4260
cgtcgatttt tgtgatgctc gtcaggggggg cggagcctat ggaaaaacgc cagcaacgcg   4320
gcctttttac ggttcctggc cttttgctgg ccttttgctc acatgttctt tcctgcgtta   4380
tcccctgatt ctgtggataa ccgtattacc gcctttgagt gagctgatac cgctcgccgc   4440
agccgaacga ccgagcgcag cgagtcagtg agcgaggaag cggaagagcg cccaatacgc   4500
aaaccgcctc tccccgcgcg ttggccgatt cattaatgca gcagctgcgc gctcgctcgc   4560
tcactgaggc cgcccgggca aagcccgggc gtcgggcgac ctttggtcgc ccggcctcag   4620
tgagcgagcg agcgcgcaga gagggagtgg ccaactccat cactaggggt tccttgtagt   4680
taatgattaa cccgccatgc tacttatcta cgtagccatg ctctaggaca ttgattattg   4740
actagtggag ttccgcgtta cataacttac ggtaaatggc ccgcctggct gaccgcccaa   4800
cgacccccgc ccattgacgt caataatgac gtatgttccc atagtaacgc caatagggac   4860
tttccattga cgtcaatggg tggagtattt acggtaaact gcccacttgg cagtacatca   4920
agtgtatcat atgccaagta cgccccctat tgacgtcaat gacggtaaat ggcccgcctg   4980
gcattatgcc cagtacatga ccttatggga ctttcctact tggcagtaca tctacgtatt   5040
agtcatcgct attaccatgg tcgaggtgag ccccacgttc tgcttcactc tccccatctc   5100
ccccccctcc ccacccccaa ttttgtattt atttattttt taattatttt gtgcagcgat   5160
ggggggcgggg gggggggggg gcgcgcgcca ggcggggcgg ggcggggcga ggggcggggc   5220
ggggcgaggc ggagaggtgc ggcggcagcc aatcagagcg cgcgctccg aaagtttcct   5280
```

-continued

```
tttatggcga ggcggcggcg gcggcggccc tataaaaagc gaagcgcgcg gcgggcggga  5340
gtcgctgcgc gctgccttcg ccccgtgccc cgctccgccg ccgcctcgcg ccgcccgccc  5400
cggctctgac tgaccgcgtt actaaaacag gtaagtccgg cctccgcgcc gggttttggc  5460
gcctcccgcg ggcgcccccc tcctcacggc gagcgctgcc acgtcagacg aagggcgcag  5520
cgagcgtcct gatccttccg cccggacgct caggacagcg gcccgctgct cataagactc  5580
ggccttagaa ccccagtatc agcagaagga cattttagga cgggacttgg gtgactctag  5640
ggcactggtt ttctttccag agagcggaac aggcgaggaa aagtagtccc ttctcggcga  5700
ttctgcggag ggatctccgt ggggcggtga acgccgatga tgcctctact aaccatgttc  5760
atgttttctt ttttttctta caggtcctgg gtgacgaaca gggtaccgcc accatggcca  5820
ccggctctcg cacaagcctg ctgctggctt tcggactgct gtgcctgcct tggctccagg  5880
agggctccgc cgctagcatc gataccgtcg ctatgtgctg gaggcttgct gaaggctgta  5940
tgctgaacag ttcttctgcg catcgttcgt tttggcctct gactgacgaa cgatgcggaa  6000
gaactgttca ggacacaagg cctgttacta gcactcacat ggaacaaatg gcctctagcc  6060
tggaggcttg ctgaaggctg tatgctgaca taatacgcat atcgctatcc gttttggcct  6120
ctgactgacg gatagcgatg cgtattatgt caggacacaa ggcctgttac tagcactcac  6180
atggaacaaa tggcctctag cctggaggct tgctgaaggc tgtatgctgt ttcttcttcg  6240
aactgctgtt gcgttttggc ctctgactga cgcaacagca gcgaagaaga aacaggacac  6300
aaggcctgtt actagcactc acatggaaca aatggcctc                         6339
```

COMPOSITION FOR REGULATING PRODUCTION OF INTERFERING RIBONUCLEIC ACID

This application contains a Sequence Listing electronically submitted via Patent Center to the United States Patent and Trademark Office as an XML Document file entitled "G10074847P1US-SequenceListing.xml" created on 2025 Sep. 3 and having a size of 15,920 bytes. The information contained in the Sequence Listing is incorporated by reference herein.

TECHNICAL FIELD

The present disclosure generally relates to compositions for regulating the production of micro-interfering ribonucleic acid (miRNA). In particular, the present disclosure relates to compositions for regulating gene expression and consequently, the production of miRNA that will suppress the expression of platelet-derived growth factor receptor beta (PDGFRB).

BACKGROUND

Platelet-derived growth factor receptor beta (PDGFRB) is a cell surface receptor tyrosine kinase protein that regulates cell growth by binding to platelet-derived growth factor.

Excessive expression of PDGFRB can promote tumour growth.

As such, it may be desirable to establish therapies, treatments and/or interventions that reduce PDGFRB expression in order to prevent or treat diseases caused by excessive PDGFRB expression.

SUMMARY

Some embodiments of the present disclosure relate to one or more compositions that upregulate the production of one or more sequences of micro-interfering ribonucleic acid (miRNA). The sequences of miRNA may be complimentary to a sequence of target messenger RNA (mRNA) that encodes for the translation of a target biomolecule, and the miRNA can cause the target mRNA to be degraded or inactivated, thereby causing a decrease in the bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is a molecule such as PDGFRB.

In some embodiments of the present disclosure, the compositions comprise a plasmid of deoxyribonucleic acid (DNA) that includes one or more insert sequences of nucleotides that encode for the production of miRNA and a backbone sequence of nucleic acids that facilitates the introduction of the one or more insert sequences into one or more of a subject's cells where it is expressed and/or replicated. Expression of the one or more insert sequences by one or more cells of the subject results in an increased production of the miRNA and, therefore, decreased translation and/or production of the target biomolecule by one or more of the subject's cells.

Some embodiments of the present disclosure relate to compositions that upregulate the production of miRNA that degrades, or causes degradation of, or inactivates, or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences that encode a miRNA sequence that targets the mRNA of PDGFRB.

Some embodiments of the present disclosure relate to a method of making a composition/target cell complex. The method comprises a step of administering an RP comprising SEQ ID NO. 1 and SEQ ID NO. 2 to a target cell in order to form the composition/target cell complex, wherein the composition/target cell complex causes the target cell to increase the production of one or more sequences of miRNA that decreases the production of a target biomolecule.

Embodiments of the present disclosure relate to at least one approach for inducing the endogenous production of one or more sequences of miRNA that target and silence mRNA of a target biomolecule, for example PDGFRB. A first approach utilizes gene vectors containing nucleotide sequences for increasing the endogenous production of one or more sequences of miRNA, which are complete or partial sequences and/or combinations thereof, that target and silence the mRNA of PDGFRB, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a kinase that is found within a subject. A biomolecule may be endogenous or exogenous to a subject and when bioavailable the biomolecule may suppress, influence or stimulate a physiological process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target biomolecule protein is produced.

In some embodiments of the present disclosure, the target biomolecule is PDGFRB.

In some embodiments of the present disclosure, the insert comprises one or more nucleotide sequences that each encode one or more miRNA sequences that may be complimentary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complimentary to and degrade, or cause degradation of, one biomolecule, such as PDGFRB. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that subsequently cause an increased production of one or more miRNA sequences that are each complimentary to and degrade, or cause degradation of, or inactivate, or cause inactivation of, one biomolecule, such as PDGFRB.

In some embodiments of the present disclosure, the delivery vehicle of the RP used for gene therapy may be a virus that can be enveloped, or not (unenveloped), replication effective, or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus *Dependoparvovirus*. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ $TCID_{50}$/kg (50% tissue culture infective dose per kilogram of the patient's body mass). In some embodiments of the present disclosure, the therapeutically effective amount of the composition that is administered to the patient is about $1 \times 10^{13}$ $TCID_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1 \times 10^{16}$ TCP/kg.

Some embodiments of the present disclosure relate to an adeno-associated virus (AAV) genome consisting of an RP that, when operable inside a target cell, will cause the target cell to produce a miRNA sequence that downregulates the production of a biomolecule, with an example being PDG-FRB. The RP is comprised of AAV2 inverted terminal repeats (ITRs), a composite CASI promoter, a human growth hormone (HGH) signal peptide followed by a miRNA expression cassette containing up to six different miRNAs targeting the mRNA of PDGFRB, followed by a Woodchuck Hepatitis Virus post-transcriptional regulatory element (WPRE) and an SV40 polyA signal.

```
SEQ ID NO. 1 (backbone sequence No. 1):
5'

TCTAGAATAATCAACCTCTGGATTACAAAATTTGTGAAAGATTGACTGGTATTCTTA

ACTATGTTGCTCCTTTTACGCTATGTGGATACGCTGCTTTAATGCCTTTGTATCATGC

TATTGCTTCCCGTATGGCTTTCATTTTCTCCTCCTTGTATAAATCCTGGTTGCTGTCTC

TTTATGAGGAGTTGTGGCCCGTTGTCAGGCAACGTGGCGTGGTGTGCACTGTGTTTG

CTGACGCAACCCCCACTGGTTGGGGCATTGCCACCACCTGTCAGCTCCTTTCCGGGA

CTTTCGCTTTCCCCCTCCCTATTGCCACGGCGGAACTCATCGCCGCCTGCCTTGCCCG

CTGCTGGACAGGGGCTCGGCTGTTGGGCACTGACAATTCCGTGGTGTTGTCGGGGAA

ATCATCGTCCTTTCCTTGGCTGCTCGCCTGTGTTGCCACCTGGATTCTGCGCGGGACG

TCCTTCTGCTACGTCCCTTCGGCCCTCAATCCAGCGGACCTTCCTTCCCGCGGCCTGC

TGCCGGCTCTGCGGCCTCTTCCGCGTCTTCGCCTTCGCCCTCAGACGAGTCGGATCTC

CCTTTGGGCCGCCTCCCCGCCTAAGCTTATCGATACCGTCGAGATCTAACTTGTTTAT

TGCAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATCAT

GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

GGGCGGCCTCAGTGAGCGAGCGAGCGCGCAGCTGGCGTAATAGCGAAGAGGCCCG

CACCGATCGCCCTTCCCAACAGTTGCGCAGCCTGAATGGCGAATGGCGATTCCGTTG
```

-continued

```
CAATGGCTGGCGGTAATATTGTTCTGGATATTACCAGCAAGGCCGATAGTTTGAGTT

CTTCTACTCAGGCAAGTGATGTTATTACTAATCAAAGAAGTATTGCGACAACGGTTA

ATTTGCGTGATGGACAGACTCTTTTACTCGGTGGCCTCACTGATTATAAAAACACTT

CTCAGGATTCTGGCGTACCGTTCCTGTCTAAAATCCCTTTAATCGGCCTCCTGTTTAG

CTCCCGCTCTGATTCTAACGAGGAAAGCACGTTATACGTGCTCGTCAAAGCAACCAT

AGTACGCGCCCTGTAGCGGCGCATTAAGCGCGGCGGGTGTGGTGGTTACGCGCAGC

GTGACCGCTACACTTGCCAGCGCCCTAGCGCCCGCTCCTTTCGCTTTCTTCCCTTCCT

TTCTCGCCACGTTCGCCGGCTTTCCCCGTCAAGCTCTAAATCGGGGGCTCCCTTTAGG

GTTCCGATTTAGTGCTTTACGGCACCTCGACCCCAAAAAACTTGATTAGGGTGATGG

TTCACGTAGTGGGCCATCGCCCTGATAGACGGTTTTTCGCCCTTTGACGTTGGAGTCC

ACGTTCTTTAATAGTGGACTCTTGTTCCAAACTGGAACAACACTCAACCCTATCTCG

GTCTATTCTTTTGATTTATAAGGGATTTTGCCGATTTCGGCCTATTGGTTAAAAAATG

AGCTGATTTAACAAAAATTTAACGCGAATTTTAACAAAATATTAACGTTTACAATTT

AAATATTTGCTTATACAATCTTCCTGTTTTTGGGGCTTTTCTGATTATCAACCGGGGT

ACATATGATTGACATGCTAGTTTTACGATTACCGTTCATCGATTCTCTTGTTTGCTCC

AGACTCTCAGGCAATGACCTGATAGCCTTTGTAGAGACCTCTCAAAAATAGCTACCC

TCTCCGGCATGAATTTATCAGCTAGAACGGTTGAATATCATATTGATGGTGATTTGA

CTGTCTCCGGCCTTTCTCACCCGTTTGAATCTTTACCTACACATTACTCAGGCATTGC

ATTTAAAATATATGAGGGTTCTAAAAATTTTTATCCTTGCGTTGAAATAAAGGCTTCT

CCCGCAAAAGTATTACAGGGTCATAATGTTTTTGGTACAACCGATTTAGCTTTATGC

TCTGAGGCTTTATTGCTTAATTTTGCTAATTCTTTGCCTTGCCTGTATGATTTATTGGA

TGTTGGAATTCCTGATGCGGTATTTTCTCCTTACGCATCTGTGCGGTATTTCACACCG

CATATGGTGCACTCTCAGTACAATCTGCTCTGATGCCGCATAGTTAAGCCAGCCCCG

ACACCCGCCAACACCCGCTGACGCGCCCTGACGGGCTTGTCTGCTCCCGGCATCCGC

TTACAGACAAGCTGTGACCGTCTCCGGGAGCTGCATGTGTCAGAGGTTTTCACCGTC

ATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCG

CGGAACCCCTATTTGTTTATTTTTCTAAATACATTCAAATATGTATCCGCTCATGAGA

CAATAACCCTGATAAATGCTTCAATAATATTGAAAAAGGAAGAGTATGAGTATTCA

ACATTTCCGTGTCGCCCTTATTCCCTTTTTTGCGGCATTTTGCCTTCCTGTTTTTGCTC

ACCCAGAAACGCTGGTGAAAGTAAAAGATGCTGAAGATCAGTTGGGTGCACGAGTG

GGTTACATCGAACTGGATCTCAACAGCGGTAAGATCCTTGAGAGTTTTCGCCCCGAA

GAACGTTTTCCAATGATGAGCACTTTTAAAGTTCTGCTATGTGGCGCGGTATTATCCC

GTATTGACGCCGGGCAAGAGCAACTCGGTCGCCGCATACACTATTCTCAGAATGACT

TGGTTGAGTACTCACCAGTCACAGAAAAGCATCTTACGGATGGCATGACAGTAAGA

GAATTATGCAGTGCTGCCATAACCATGAGTGATAACACTGCGGCCAACTTACTTCTG

ACAACGATCGGAGGACCGAAGGAGCTAACCGCTTTTTTGCACAACATGGGGGATCA

TGTAACTCGCCTTGATCGTTGGGAACCGGAGCTGAATGAAGCCATACCAAACGACG

AGCGTGACACCACGATGCCTGTAGCAATGGCAACAACGTTGCGCAAACTATTAACT

GGCGAACTACTTACTCTAGCTTCCCGGCAACAATTAATAGACTGGATGGAGGCGGAT

AAAGTTGCAGGACCACTTCTGCGCTCGGCCCTTCCGGCTGGCTGGTTTATTGCTGAT
```

-continued

```
AAATCTGGAGCCGGTGAGCGTGGGTCTCGCGGTATCATTGCAGCACTGGGGCCAGA

TGGTAAGCCCTCCCGTATCGTAGTTATCTACACGACGGGGAGTCAGGCAACTATGGA

TGAACGAAATAGACAGATCGCTGAGATAGGTGCCTCACTGATTAAGCATTGGTAAC

TGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACG

TGAGTTTTCGTTCCACTGAGCGTCAGACCCCGTAGAAAAGATCAAAGGATCTTCTTG

AGATCCTTTTTTTCTGCGCGTAATCTGCTGCTTGCAAACAAAAAAACCACCGCTACC

AGCGGTGGTTTGTTTGCCGGATCAAGAGCTACCAACTCTTTTTCCGAAGGTAACTGG

CTTCAGCAGAGCGCAGATACCAAATACTGTCCTTCTAGTGTAGCCGTAGTTAGGCCA

CCACTTCAAGAACTCTGTAGCACCGCCTACATACCTCGCTCTGCTAATCCTGTTACC

AGTGGCTGCTGCCAGTGGCGATAAGTCGTGTCTTACCGGGTTGGACTCAAGACGATA

GTTACCGGATAAGGCGCAGCGGTCGGGCTGAACGGGGGGTTCGTGCACACAGCCCA

GCTTGGAGCGAACGACCTACACCGAACTGAGATACCTACAGCGTGAGCTATGAGAA

AGCGCCACGCTTCCCGAAGGGAGAAAGGCGGACAGGTATCCGGTAAGCGGCAGGG

TCGGAACAGGAGAGCGCACGAGGGAGCTTCCAGGGGGAAACGCCTGGTATCTTTAT

AGTCCTGTCGGGTTTCGCCACCTCTGACTTGAGCGTCGATTTTTGTGATGCTCGTCAG

GGGGGCGGAGCCTATGGAAAAACGCCAGCAACGCGGCCTTTTTACGGTTCCTGGCC

TTTTGCTGGCCTTTTGCTCACATGTTCTTTCCTGCGTTATCCCCTGATTCTGTGGATAA

CCGTATTACCGCCTTTGAGTGAGCTGATACCGCTCGCCGCAGCCGAACGACCGAGCG

CAGCGAGTCAGTGAGCGAGGAAGCGGAAGAGCGCCCAATACGCAAACCGCCTCTCC

CCGCGCGTTGGCCGATTCATTAATGCAGCAGCTGCGCGCTCGCTCGCTCACTGAGGC

CGCCCGGGCAAAGCCCGGGCGTCGGGCGACCTTTGGTCGCCCGGCCTCAGTGAGCG

AGCGAGCGCGCAGAGAGGGAGTGGCCAACTCCATCACTAGGGGTTCCTTGTAGTTA

ATGATTAACCCGCCATGCTACTTATCTACGTAGCCATGCTCTAGGACATTGATTATTG

ACTAGTGGAGTTCCGCGTTACATAACTTACGGTAAATGGCCCGCCTGGCTGACCGCC

CAACGACCCCCGCCCATTGACGTCAATAATGACGTATGTTCCCATAGTAACGCCAAT

AGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGACGGTAA

ATGGCCCGCCTGGCATTATGCCCAGTACATGACCTTATGGGACTTTCCTACTTGGCA

GTACATCTACGTATTAGTCATCGCTATTACCATGGTCGAGGTGAGCCCCACGTTCTG

CTTCACTCTCCCCATCTCCCCCCCCTCCCCACCCCCAATTTTGTATTTATTTATTTTTT

AATTATTTTGTGCAGCGATGGGGGGGGGGGGGGGGGGGCGCGCGCCAGGCGGG

GCGGGGCGGGGCGAGGGGCGGGGCGGGGCGAGGCGGAGAGGTGCGGCGGCAGCCA

ATCAGAGCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCTTCGCCC

CGTGCCCCGCTCCGCCGCCGCCTCGCGCCGCCCGCCCCGGCTCTGACTGACCGCGTT

ACTAAAACAGGTAAGTCCGGCCTCCGCGCCGGGTTTTGGCGCCTCCCGCGGGCGCCC

CCCTCCTCACGGCGAGCGCTGCCACGTCAGACGAAGGGCGCAGCGAGCGTCCTGAT

CCTTCCGCCCGGACGCTCAGGACAGCGGCCCGCTGCTCATAAGACTCGGCCTTAGAA

CCCCAGTATCAGCAGAAGGACATTTTAGGACGGGACTTGGGTGACTCTAGGGCACT
```

-continued

GGTTTTCTTTCCAGAGAGCGGAACAGGCGAGGAAAAGTAGTCCCTTCTCGGCGATTC

TGCGGAGGGATCTCCGTGGGGCGGTGAACGCCGATGATGCCTCTACTAACCATGTTC

ATGTTTTCTTTTTTTTTCTACAGGTCCTGGGTGACGAACAGGGTACC

3'

SEQ ID NO. 2 (miRNA expression cassette No. 2 - PDGFRB):
5'

GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGG

AGGCTTGCTGAAGGCTGTATGCTGAACAGTTCTTCTGCGCATCGTTCGTTTTGGCCTC

TGACTGACGAACGATGCGGAAGAACTGTTCAGGACACAAGGCCTGTTACTAGCACT

CACATGGAACAAATGGCCTCTAGCCTGGAGGCTTGCTGAAGGCTGTATGCTGACATA

ATACGCATATCGCTATCCGTTTTGGCCTCTGACTGACGGATAGCGATGCGTATTATG

TCAGGACACAAGGCCTGTTACTAGCACTCACATGGAACAAATGGCCTCTAGCCTGG

AGGCTTGCTGAAGGCTGTATGCTGTTTCTTCTTCGAACTGCTGTTGCGTTTTGGCCTC

TGACTGACGCAACAGCAGCGAAGAAGAAACAGGACACAAGGCCTGTTACTAGCACT

CACATGGAACAAATGGCCTC

3'

SEQ ID NO. 3 = SEQ ID NO. 1 + SEQ ID NO. 2
5'

TCTAGAATAATCAACCTCTGGATTACAAAATTTGTGAAAGATTGACTGGTATTCTTA

ACTATGTTGCTCCTTTTACGCTATGTGGATACGCTGCTTTAATGCCTTTGTATCATGC

TATTGCTTCCCGTATGGCTTTCATTTTCTCCTCCTTGTATAAATCCTGGTTGCTGTCTC

TTTATGAGGAGTTGTGGCCCGTTGTCAGGCAACGTGGCGTGGTGTGCACTGTGTTTG

CTGACGCAACCCCCACTGGTTGGGGCATTGCCACCACCTGTCAGCTCCTTTCCGGGA

CTTTCGCTTTCCCCCTCCCTATTGCCACGGCGGAACTCATCGCCGCCTGCCTTGCCCG

CTGCTGGACAGGGGCTCGGCTGTTGGGCACTGACAATTCCGTGGTGTTGTCGGGGAA

ATCATCGTCCTTTCCTTGGCTGCTCGCCTGTGTTGCCACCTGGATTCTGCGCGGGACG

TCCTTCTGCTACGTCCCTTCGGCCCTCAATCCAGCGGACCTTCCTTCCCGCGGCCTGC

TGCCGGCTCTGCGGCCTCTTCCGCGTCTTCGCCTTCGCCCTCAGACGAGTCGGATCTC

CCTTTGGGCCGCCTCCCCGCCTAAGCTTATCGATACCGTCGAGATCTAACTTGTTTAT

TGCAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATCAT

GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

GGGCGGCCTCAGTGAGCGAGCGAGCGCGCAGCTGGCGTAATAGCGAAGAGGCCCG

CACCGATCGCCCTTCCCAACAGTTGCGCAGCCTGAATGGCGAATGGCGATTCCGTTG

CAATGGCTGGCGGTAATATTGTTCTGGATATTACCAGCAAGGCCGATAGTTTGAGTT

CTTCTACTCAGGCAAGTGATGTTATTACTAATCAAAGAAGTATTGCGACAACGGTTA

ATTTGCGTGATGGACAGACTCTTTTACTCGGTGGCCTCACTGATTATAAAAACACTT

CTCAGGATTCTGGCGTACCGTTCCTGTCTAAAATCCCTTTAATCGGCCTCCTGTTTAG

CTCCCGCTCTGATTCTAACGAGGAAAGCACGTTATACGTGCTCGTCAAAGCAACCAT

-continued

```
AGTACGCGCCCTGTAGCGGCGCATTAAGCGCGGCGGGTGTGGTGGTTACGCGCAGC

GTGACCGCTACACTTGCCAGCGCCCTAGCGCCCGCTCCTTTCGCTTTCTTCCCTTCCT

TTCTCGCCACGTTCGCCGGCTTTCCCCGTCAAGCTCTAAATCGGGGGCTCCCTTTAGG

GTTCCGATTTAGTGCTTTACGGCACCTCGACCCCAAAAAACTTGATTAGGGTGATGG

TTCACGTAGTGGGCCATCGCCCTGATAGACGGTTTTTCGCCCTTTGACGTTGGAGTCC

ACGTTCTTTAATAGTGGACTCTTGTTCCAAACTGGAACAACACTCAACCCTATCTCG

GTCTATTCTTTTGATTTATAAGGGATTTTGCCGATTTCGGCCTATTGGTTAAAAAATG

AGCTGATTTAACAAAAATTTAACGCGAATTTTAACAAAATATTAACGTTTACAATTT

AAATATTTGCTTATACAATCTTCCTGTTTTTGGGGCTTTTCTGATTATCAACCGGGGT

ACATATGATTGACATGCTAGTTTTACGATTACCGTTCATCGATTCTCTTGTTTGCTCC

AGACTCTCAGGCAATGACCTGATAGCCTTTGTAGAGACCTCTCAAAAATAGCTACCC

TCTCCGGCATGAATTTATCAGCTAGAACGGTTGAATATCATATTGATGGTGATTTGA

CTGTCTCCGGCCTTTCTCACCCGTTTGAATCTTTACCTACACATTACTCAGGCATTGC

ATTTAAAATATATGAGGGTTCTAAAAATTTTTATCCTTGCGTTGAAATAAAGGCTTCT

CCCGCAAAAGTATTACAGGGTCATAATGTTTTTGGTACAACCGATTTAGCTTTATGC

TCTGAGGCTTTATTGCTTAATTTTGCTAATTCTTTGCCTTGCCTGTATGATTTATTGGA

TGTTGGAATTCCTGATGCGGTATTTTCTCCTTACGCATCTGTGCGGTATTTCACACCG

CATATGGTGCACTCTCAGTACAATCTGCTCTGATGCCGCATAGTTAAGCCAGCCCCG

ACACCCGCCAACACCCGCTGACGCGCCCTGACGGGCTTGTCTGCTCCCGGCATCCGC

TTACAGACAAGCTGTGACCGTCTCCGGGAGCTGCATGTGTCAGAGGTTTTCACCGTC

ATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCG

CGGAACCCCTATTTGTTTATTTTTCTAAATACATTCAAATATGTATCCGCTCATGAGA

CAATAACCCTGATAAATGCTTCAATAATATTGAAAAAGGAAGAGTATGAGTATTCA

ACATTTCCGTGTCGCCCTTATTCCCTTTTTTGCGGCATTTTGCCTTCCTGTTTTTGCTC

ACCCAGAAACGCTGGTGAAAGTAAAAGATGCTGAAGATCAGTTGGGTGCACGAGTG

GGTTACATCGAACTGGATCTCAACAGCGGTAAGATCCTTGAGAGTTTTCGCCCCGAA

GAACGTTTTCCAATGATGAGCACTTTTAAAGTTCTGCTATGTGGCGCGGTATTATCCC

GTATTGACGCCGGGCAAGAGCAACTCGGTCGCCGCATACACTATTCTCAGAATGACT

TGGTTGAGTACTCACCAGTCACAGAAAAGCATCTTACGGATGGCATGACAGTAAGA

GAATTATGCAGTGCTGCCATAACCATGAGTGATAACACTGCGGCCAACTTACTTCTG

ACAACGATCGGAGGACCGAAGGAGCTAACCGCTTTTTTGCACAACATGGGGGATCA

TGTAACTCGCCTTGATCGTTGGGAACCGGAGCTGAATGAAGCCATACCAAACGACG

AGCGTGACACCACGATGCCTGTAGCAATGGCAACAACGTTGCGCAAACTATTAACT

GGCGAACTACTTACTCTAGCTTCCCGGCAACAATTAATAGACTGGATGGAGGCGGAT

AAAGTTGCAGGACCACTTCTGCGCTCGGCCCTTCCGGCTGGCTGGTTTATTGCTGAT

AAATCTGGAGCCGGTGAGCGTGGGTCTCGCGGTATCATTGCAGCACTGGGGCCAGA

TGGTAAGCCCTCCCGTATCGTAGTTATCTACACGACGGGGAGTCAGGCAACTATGGA

TGAACGAAATAGACAGATCGCTGAGATAGGTGCCTCACTGATTAAGCATTGGTAAC

TGTCAGACCAAGTTTACTCATATATACTTTAGATTGATTTAAAACTTCATTTTTAATT
```

-continued

TAAAAGGATCTAGGTGAAGATCCTTTTTGATAATCTCATGACCAAAATCCCTTAACG

TGAGTTTTCGTTCCACTGAGCGTCAGACCCCGTAGAAAAGATCAAAGGATCTTCTTG

AGATCCTTTTTTTCTGCGCGTAATCTGCTGCTTGCAAACAAAAAAACCACCGCTACC

AGCGGTGGTTTGTTTGCCGGATCAAGAGCTACCAACTCTTTTTCCGAAGGTAACTGG

CTTCAGCAGAGCGCAGATACCAAATACTGTCCTTCTAGTGTAGCCGTAGTTAGGCCA

CCACTTCAAGAACTCTGTAGCACCGCCTACATACCTCGCTCTGCTAATCCTGTTACC

AGTGGCTGCTGCCAGTGGCGATAAGTCGTGTCTTACCGGGTTGGACTCAAGACGATA

GTTACCGGATAAGGCGCAGCGGTCGGGCTGAACGGGGGGTTCGTGCACACAGCCCA

GCTTGGAGCGAACGACCTACACCGAACTGAGATACCTACAGCGTGAGCTATGAGAA

AGCGCCACGCTTCCCGAAGGGAGAAAGGCGGACAGGTATCCGGTAAGCGGCAGGG

TCGGAACAGGAGAGCGCACGAGGGAGCTTCCAGGGGGAAACGCCTGGTATCTTTAT

AGTCCTGTCGGGTTTCGCCACCTCTGACTTGAGCGTCGATTTTTGTGATGCTCGTCAG

GGGGGCGGAGCCTATGGAAAAACGCCAGCAACGCGGCCTTTTTACGGTTCCTGGCC

TTTTGCTGGCCTTTTGCTCACATGTTCTTTCCTGCGTTATCCCCTGATTCTGTGGATAA

CCGTATTACCGCCTTTGAGTGAGCTGATACCGCTCGCCGCAGCCGAACGACCGAGCG

CAGCGAGTCAGTGAGCGAGGAAGCGGAAGAGCGCCCAATACGCAAACCGCCTCTCC

CCGCGCGTTGGCCGATTCATTAATGCAGCAGCTGCGCGCTCGCTCGCTCACTGAGGC

CGCCCGGGCAAAGCCCGGGCGTCGGGCGACCTTTGGTCGCCCGGCCTCAGTGAGCG

AGCGAGCGCGCAGAGAGGGAGTGGCCAACTCCATCACTAGGGGTTCCTTGTAGTTA

ATGATTAACCCGCCATGCTACTTATCTACGTAGCCATGCTCTAGGACATTGATTATTG

ACTAGTGGAGTTCCGCGTTACATAACTTACGGTAAATGGCCCGCCTGGCTGACCGCC

CAACGACCCCCGCCCATTGACGTCAATAATGACGTATGTTCCCATAGTAACGCCAAT

AGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGACGGTAA

ATGGCCCGCCTGGCATTATGCCCAGTACATGACCTTATGGGACTTTCCTACTTGGCA

GTACATCTACGTATTAGTCATCGCTATTACCATGGTCGAGGTGAGCCCCACGTTCTG

CTTCACTCTCCCCATCTCCCCCCCCTCCCCACCCCCAATTTTGTATTTATTTATTTTTT

AATTATTTTGTGCAGCGATGGGGGCGGGGGGGGGGGGGGCGCGCGCCAGGCGGG

GCGGGGCGGGGCGAGGGGGGGGCGGGGCGAGGCGGAGAGGTGCGGCGGCAGCCA

ATCAGAGCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCTTCGCCC

CGTGCCCCGCTCCGCCGCCGCCTCGCGCCGCCCGCCCCGGCTCTGACTGACCGCGTT

ACTAAAACAGGTAAGTCCGGCCTCCGCGCCGGGTTTTGGCGCCTCCCGCGGGCGCCC

CCCTCCTCACGGCGAGCGCTGCCACGTCAGACGAAGGGCGCAGCGAGCGTCCTGAT

CCTTCCGCCCGGACGCTCAGGACAGCGGCCCGCTGCTCATAAGACTCGGCCTTAGAA

CCCCAGTATCAGCAGAAGGACATTTTAGGACGGGACTTGGGTGACTCTAGGGCACT

GGTTTTCTTTCCAGAGAGCGGAACAGGCGAGGAAAAGTAGTCCCTTCTCGGCGATTC

TGCGGAGGGATCTCCGTGGGGCGGTGAACGCCGATGATGCCTCTACTAACCATGTTC

ATGTTTTCTTTTTTTTTCTACAGGTCCTGGGTGACGAACAGGGTACCGCCACCATGGC

CACCGGCTCTCGCACAAGCCTGCTGCTGGCTTTCGGACTGCTGTGCCTGCCTTGGCT

CCAGGAGGGCTCCGCCGCTAGCATCGATACCGTCGCTATGTGCTGGAGGCTTGCTGA

-continued

AGGCTGTATGCTGAACAGTTCTTCTGCGCATCGTTCGTTTTGGCCTCTGACTGACGAA

CGATGCGGAAGAACTGTTCAGGACACAAGGCCTGTTACTAGCACTCACATGGAACA

AATGGCCTCTAGCCTGGAGGCTTGCTGAAGGCTGTATGCTGACATAATACGCATATC

GCTATCCGTTTTGGCCTCTGACTGACGGATAGCGATGCGTATTATGTCAGGACACAA

GGCCTGTTACTAGCACTCACATGGAACAAATGGCCTCTAGCCTGGAGGCTTGCTGAA

GGCTGTATGCTGTTTCTTCTTCGAACTGCTGTTGCGTTTTGGCCTCTGACTGACGCAA

CAGCAGCGAAGAAGAAACAGGACACAAGGCCTGTTACTAGCACTCACATGGAACA

AATGGCCTC

3'

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 3, or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands of interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR, CASI promoter, miRNA expression cassette, WPRE, SV40 polyA and ITR 3'.

Example 2—In Vitro Studies

To confirm that the recombinant plasmid of Example 1 works to downregulate PDGFRB expression, HEK293 cells were treated with either a first plasmid (the First Treatment) or the first plasmid in combination with a second plasmid (collectively, the Second Treatment).

The First Treatment comprised the first plasmid with a nucleotide sequence that codes for the backbone nucleotide sequence No. 1 (described herein as SEQ ID NO. 1) and a nucleotide sequence that codes for the expression of the first 1,800 nucleotides of PDGFRB receptor mRNA of the sequence defined in Uniprot P09619.PGFRB_HUMAN. HEK293 cells do not produce substantial amounts of PDGFRB receptor on their own and, therefore, the purpose of the First Treatment was to cause the HEK293 cells to produce enough of a fragment of PDGFRB receptor so that any decrease in the fragment of PDGFRB receptor production caused by the Second Treatment could be detected.

The Second Treatment comprised the first plasmid (which included the nucleotide sequence of SEQ ID NO. 1 and a nucleotide sequence that codes for expression of the first 1,800 nucleotides of PDGFRB receptor mRNA) and the second plasmid, which coded for the backbone nucleotide sequence SEQ ID NO. 1 and a nucleotide sequence of the micro-interfering RNA (miRNA) for PDGFRB receptors (described herein as SEQ ID NO. 2). SEQ ID NO. 2 codes for a miRNA sequence that is designed to bind to and inactivate the messenger ribonucleic acid (mRNA) of VEGF receptors.

Briefly, the HEK293 cells were seeded in 96-wellplates in Dulbecco's Modified Eagle Medium (DMEM)/10% Fetal Bovine Serum (FBS) media. 24 hours later, the cells were treated with either the First Treatment or the Second Treatment. A transfection mixture containing OptiMEM (reduced serum medium, commercially available from Gibco), plasmid DNA, and PEI max (Transfection Grade Linear Polyethylenimine Hydrochloride (MW 40,000), commercially available from Polysciences) was prepared in a sterile 1 mL conical tube and incubated at room temperature for 10 minutes prior to adding 100 μL of the mixture to each seeded well (100 L/well equals about 1 μg of each plasmid per well).

72 hours post-treatment, the cells were harvested by separating the cells from the well surface with 2.9 mM ethylenediaminetetraacetic acid (EDTA) and centrifuging the resulting cell suspension into a cell pellet. The cell pellet was lysed, and 40 μg of protein (as assayed by the Lowry assay) was loaded into sodium dodecyl sulfate-polyacrylamide (SDS PAGE) gels for molecular weight electrophoretic separation. A total of eight gel lanes were loaded with the protein obtained from the wells treated with the First Treatment and eight gel lanes were loaded with the protein obtained from the wells treated with the Second Treatment. The band approximating 67,659 Daltons (the molecular weight of the first 600 amino acids of the PDGFRB receptor amino acid sequence), was excised from each lane, eluted, and the protein amount was assayed by the Lowry method.

The average expression levels of the fragment of PDG-FRB receptor (μg) measured in HEK293 cells treated with the First Treatment (that encoded for the fragment of VEGF receptor mRNA) was 10.7 μg. The average expression levels in the HEK293 cells treated with the Second Treatment (that encoded for SEQ ID NO. 2) was less than 1 μg, which is below the lower detection limit of the Lowry assay. The amounts of measured protein were significantly different, as assessed by a two-way T-test (p<0.001), using 1 μg as the value for the expression levels in the HEK293 cells treated with the Second Treatment.

This data demonstrates that the HEK293 cells treated with the First Treatment were successfully transfected causing the cells to produce a fragment of PDGFRB receptor, a protein HEK293 cells typically do not produce in vitro without any treatment. The data above also demonstrates that the HEK293 cells treated with the Second Treatment produced significantly less of a fragment of PDGFRB receptor.

Without being bound by any particular theory, this data demonstrates the efficacy of miRNA-based gene silencing of PDGFRB receptor protein expression by using the Second Treatment, which included the miRNA encoded by SEQ ID NO. 2.

The invention claimed is:

1. A composition that comprises a recombinant plasmid (RP) comprising a sequence of nucleotides that is SEQ ID NO. 2.

2. The composition of claim 1, wherein the RP is encapsulated in a protein coat, a lipid vesicle, or any combination thereof.

3. A composition that comprises a recombinant plasmid (RP) comprising a sequence of nucleotides that is SEQ ID NO. 3.

\* \* \* \* \*